United States Patent [19]

Scott

[11] Patent Number: 4,715,362

[45] Date of Patent: Dec. 29, 1987

[54] AMBULATORY LUMBO-SACRAL TRACTION SYSTEMS AND METHODS

[76] Inventor: Henry Scott, 1109 Rock Creek Dr., Wyncote, Pa. 19095

[21] Appl. No.: 833,705

[22] Filed: Feb. 27, 1986

[51] Int. Cl.$^4$ ............................ A61H 1/02; A61F 5/04
[52] U.S. Cl. ...................................... 128/75; 128/878; 128/78
[58] Field of Search .................. 128/78, 89 R, 69, 75, 128/82, 84 R; 248/601, 600; 2/44

[56] References Cited

U.S. PATENT DOCUMENTS

| | | | |
|---|---|---|---|
| 1,589,670 | 6/1926 | Vartia | 128/75 |
| 1,678,584 | 7/1928 | Branson | 2/44 |
| 1,722,205 | 7/1929 | Freund | 128/78 |
| 2,886,031 | 5/1959 | Robbins | 128/78 |
| 3,029,810 | 4/1962 | Martin | 2/44 |
| 3,420,230 | 1/1969 | Ballard | 128/75 |

FOREIGN PATENT DOCUMENTS 0581940 11/1977 U.S.S.R. ................. 128/78

Primary Examiner—Edgar S. Burr
Assistant Examiner—Tonya Lamb
Attorney, Agent, or Firm—Millen & White

[57] ABSTRACT

Ambulatory lumbo-sacral traction systems and methods utilize upper and lower support members in the form of belts which encircle a patient adjacent the pelvis and under the arms. The support members are held in spaced relation by struts which are longitudinally adjustable and include compression springs therein for absorbing shocks which might otherwise be transmitted to the spine.

9 Claims, 6 Drawing Figures

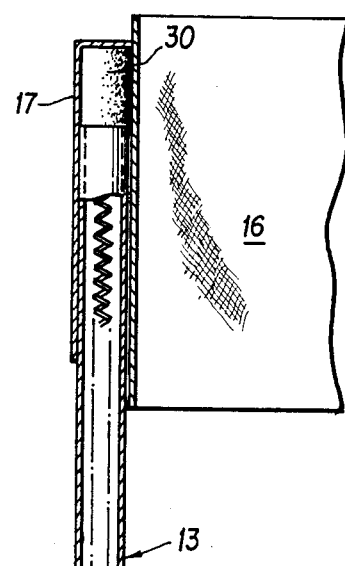
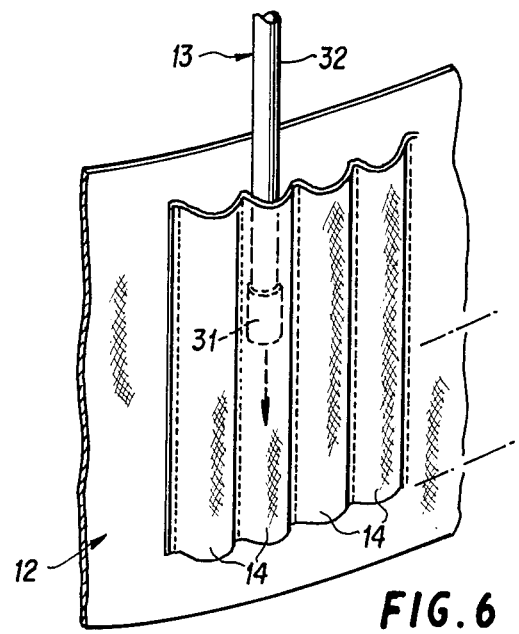
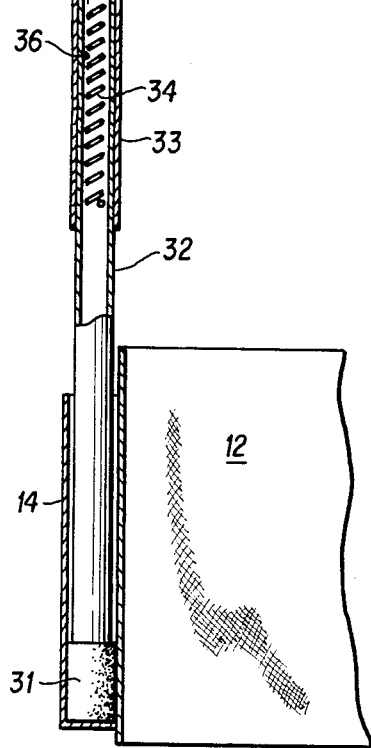
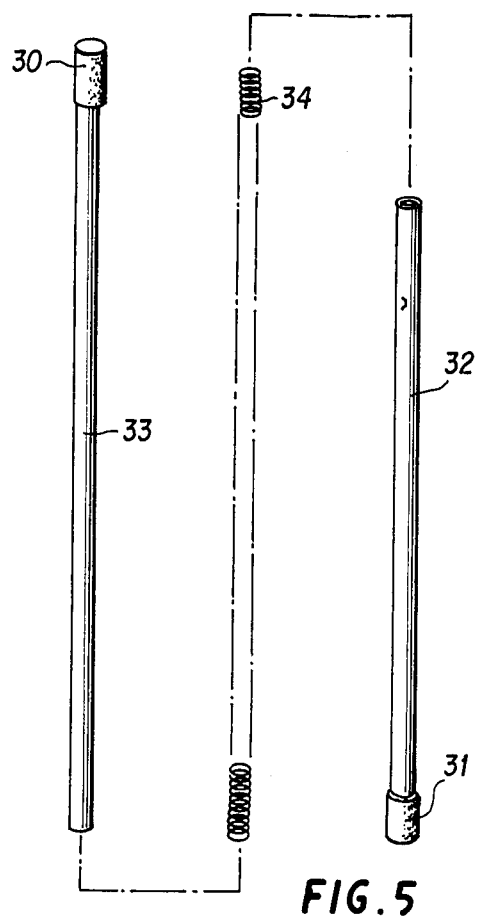
FIG. 4
FIG. 6
FIG. 5

AMBULATORY LUMBO-SACRAL TRACTION SYSTEMS AND METHODS

BACKGROUND OF THE INVENTION

1. Field of the Invention

The instant invention relates to lumbo-sacral traction systems, and more particularly, the instant invention relates to an ambulatory lumbo-sacral traction system.

2. Technical Considerations in Prior Art

Presently known systems for providing traction or otherwise removing or minimizing compressive forces on the vertebral "discs" or other cartilage or bone structure in the lumbar, sacral, or pelvic region have the severe disadvantage that they require the patient to be hospitalized or at least confined to bed or to some complicated and/or otherwise restrictive device that does not allow the patient sufficient freedom to perform productive functions or other normal activities. Consequently, the recovery period is a tedious and unproductive one, and the patient is often tempted to prematurely return to normal activities before recovery is complete. The unfortunate result is that the injured portions of the patient's spine are usually unduly strained and the patient is again required to undergo traction.

Considering the prior art approaches more specifically, the general approach is to require a patient with spinal problems alleviated by traction to lie in bed with cables attached to portions of the patient's body and sand bags or other weights attached to the cables so as to apply tension to the patient and thereby relieve compressive forces on the patient's spine. This is, of course, a highly restrictive treatment. Other approaches include systems such as that disclosed in U.S. Pat. No. 3,167,068 wherein a patient sits in a chair with an upright lumbo-sacral traction system attached to the chair. The patient is thus free to use his or her arms while undergoing traction. However, the patient is not "ambulatory." Still another approach is disclosed in U.S. Pat. No. 4,170,988 wherein the patient is suspended upside down while retained by his or her ankles. With this approach, the weight of the patient's body is used to tension the spine and thus relieve compressive forces in the spine. While the patient is suspended upside down, there is not much the patient can do. Generally, each treatment takes 5 to 10 minutes and may provide the patient with sufficient relief to perform normal activities for perhaps a day or so before the treatment must be repeated. The approach disclosed in U.S. Pat. No. 4,170,988 may from time to time have rather catastrophic side effects in that blood tends to pool in the patient's head, increasing the risk of an aneurism and possibly damage to the patient's eyes due to increased fluid pressure therein.

In view of the limitations and drawbacks of the afore-described treatments, there is a need for a traction system which permits a patient to be ambulatory while undergoing traction treatment.

SUMMARY OF THE INVENTION

It is an object of the instant invention to provide a new and improved system and a new and improved method of traction treatment wherein a patient undergoing the treatment is ambulatory.

Upon further study of the specification and appended claims, further objects and advantages of this invention will become apparent to those skilled in the art.

The instant invention contemplates upper and lower support means encircling a patient adjacent the patient's pelvis and adjacent the patient's upper back just beneath the patient's arms. The support means are held in spaced relation by strut means which extend between the support means and are received in pockets disposed in the support means.

In accordance with a preferred embodiment of the invention, the strut means includes a shock absorber and is longitudinally adjustable.

The instant invention further contemplates the method of using the afore-described system to relieve compressive stresses on the patient's spine.

BRIEF DESCRIPTION OF THE DRAWINGS.

FIG. 4 is a view of a portion of the traction system with a supporting strut partially cut away to show the interior thereof;

FIG. 5 is an exploded view of a strut; and

FIG. 6 is a perspective view of a portion of the traction system showing how a strut is removably inserted into a pocket on a belt-type support member which encircles the patient.

DESCRIPTION OF THE PREFERRED EMBODIMENT

Figure 1:
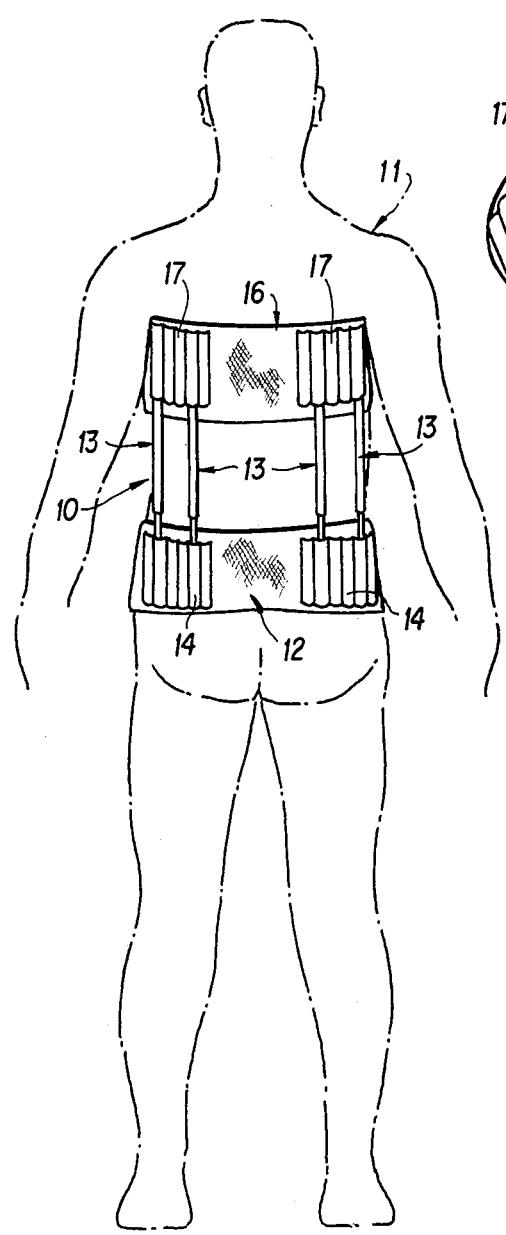
FIG. 1 is a rear view of the traction system in accordance with the instant invention attached to a patient.

Referring now to FIG. 1 there is shown a traction system, designated generally by the numeral 10, configured in accordance with principles of the instant invention and worn by a patient, designated generally by the numeral 11. The traction system includes a lower support member, designated generally by the numeral 12, which lower support member is in the form of a belt that encircles the patient 11 at a location adjacent the patient's pelvic area. Extending from the lower support 12 are two pairs of struts, each strut designated generally by the numeral 13, with each pair of the struts disposed laterally with respect to the spine of the patient. The struts 13 are received in pocket members 14 in the lower support 12. Positioned in space relation to the lower support 12 is an upper support, designated generally by the numeral 16. The upper support 16 is a belt member that encircles the body of the patient 11 at a location just beneath the patient's armpits and adjacent the patient's clavicle. The struts 13 are received in pockets 17 on the upper belt member 16 in order to positively hold the upper belt member 16 and lower belt member 12 in spaced relation to one another.

In operation, the system 10 shown in FIG. 1 provides an auxiliary support for the upper part of the patient's body 11, wherein the weight of the upper part of the body is carried by the struts 13 from the upper support 16 to the lower support 12 by the struts 13. Consequently, compressive stresses on the patient's spine are minimized or relieved. The system 10 in effect provides an exterior skeletal support which supplements the spine on an ambulatory patient.

Figure 2:
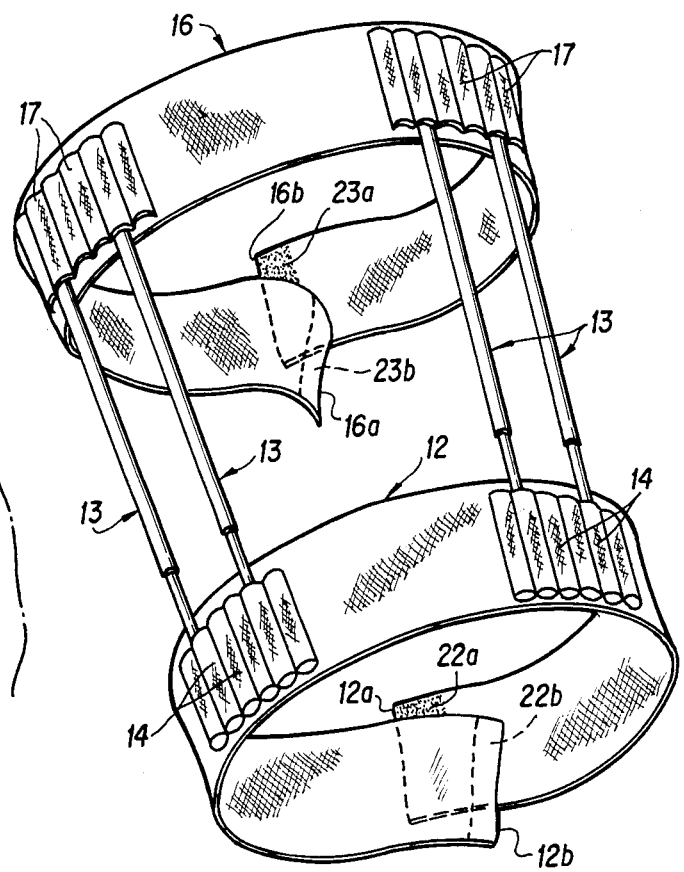
FIG. 2 is a perspective view of the traction system in accordance with the instant invention.

Referring now more specifically to FIG. 2, it is seen that the traction system 10 is configured with the lower support 12 and the upper support 16 in the form of belts which have end portions 12a and 12b and 16a and 16b, respectively, which end portions fasten together so that the belts encircle the patient's body. In accordance with a preferred embodiment of the invention, the end portions of the belts or supports 12 and 16 have complementary VELCRO surfaces 22a, 22b and 23a and 23b which adhere when pressed together.

There are a plurality of pocket members 14 on the lower support 12 and a plurality of pocket members 17 on the upper support 16. Consequently, the struts 13 can be located in various positions on the support members 16 and 12 to accomodate patients of different sizes and body configurations and can be adjusted to suit a particular patient. While a pair of struts 13 are shown mounted on either side of the patient's spine, it may in some situations be preferrable to have a single strut or perhaps more than two struts mounted on each side of the patient's spine. As seen in FIG. 6, the struts 13 are readily removable from and insertable into the pockets 14 and 17 and simply bottomed in the pockets when inserted, as is perhaps best seen in FIG. 4.

Figure 3:
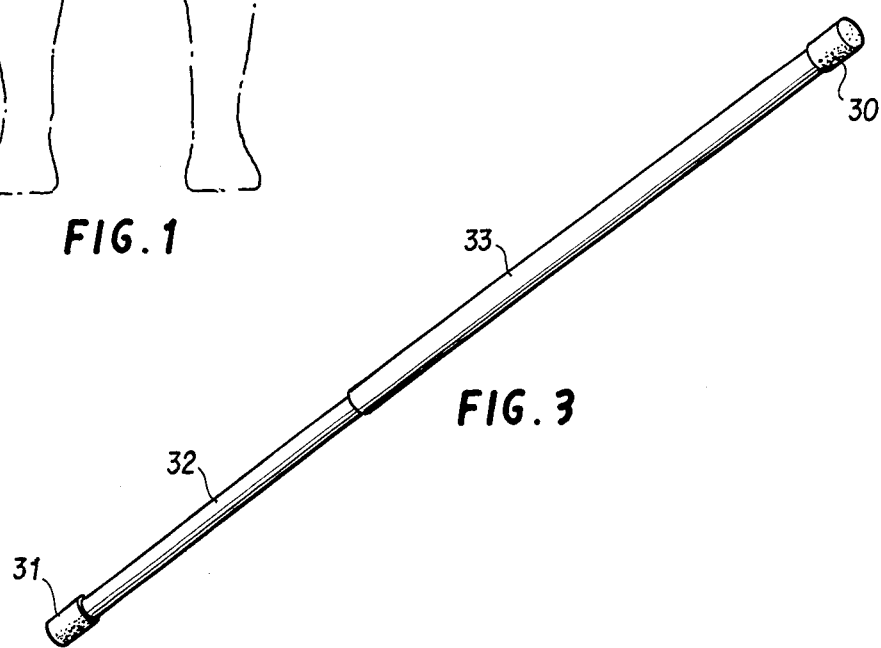
FIG. 3 is a perspective view of a strut used with the traction system of the instant invention.

Referring now to FIGS. 3, 4 and 5, the struts 13 are preferrably made of steel, or a similar rigid material, and have top and bottom caps 30 and 31 of a relatively soft material to prevent chafing of the pockets 14 and 17.

The struts 13 are tubular with an inner tube 32 telescoped within an outer tube 33. In order to determine the length of the tube, there is a spring 34 received in the tubes, the spring 34 bottoming against the bottom of the outer tube and engaging a projection 36 on the inner tube 32. By rotating the inner tube with respect to the outer tube, the projection 36 migrates longitudinally along the coil spring 34 so that the outer tube and inner tube expand longitudinally with respect to one another. The actual coupling between the outer tube 33 and the inner tube 32 is the spring 34 which is compressed if opposed longitudinal forces are applied to the outer tube 33 and the inner tube 32. Consequently, the spring 34 acts as a shock absorber to absorb at least a substantial portion of the vertical impact which would ordinarily be transmitted through the patient's spine due to the patient's upper body portions moving with respect to the patient's lower body portions as the patient walks or otherwise moves. Alternatively, the struts 13 can be made of a semiflexible plastic material.

By utilizing the traction system and traction method of the instant invention, the patient is able to walk around with his arms free and is able to sit and stand at will. The traction system can be used to apply traction to the patient's spine when the patient is reclining or when the patient is sitting or standing. Moreover, the system is readily adjustable and has the additional advantage of absorbing vertical impacts or shocks so as to minimize or eliminate pain due to spinal ailments while allowing the spine to recuperate from previous injuries.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. An ambulatory lumbo-sacral back brace for relieving upper body weight from the lower lumbo-sacral region of a patient's spine, the system comprising:
    a single upper support member for encircling the patient adjacent the patient's clavicle and beneath the patient's arms, the upper support member being in the form of a first flexible web having a back portion, a front portion and two free ends, with a first adjustable fastening means for connecting the free ends of the webs together to form a first closed loop;
    single lower support member for encircling the patient at a location adjacent the pelvis of the patient, the lower support member being in the form of a second flexible web having a back portion, a front portion, and two free ends adjacent the front portion with a second adjustable fastening means for connecting the ends of the web together to form a second closed loop;
    a plurality of substantially vertical and parallel longitudinally compressible struts having upper and lower ends, the struts each having individually adjustable internal biasing means for resisting longitudinal contraction;
    a plurality of individual strut securing pockets on each of said support members, each said support member having at least one pocket on each side of the spine, none of said pockets being aligned with the patient's spine, said pockets receiving individual struts and securing the struts between the upper and lower support members with the struts being selectively removable from the pockets, the strut securing pockets being positioned at a plurality of longitudinally spaced locations on the upper and lower support members, the spaced locations being distributed over the back portions of the webs on both side of the spine when the system is placed on a patient, each of the strut securing pockets extending laterally with respect to its respective web for securing the strut to the web adjacent both the top and bottom edge thereof to prevent the strut from pivoting with respect to the webs, whereby the struts are selectively secured to the upper and lower support members at selected longitudinal locations on the belts and are individually adjustable in longitudinal force according to the needs of the patient using the system.

2. The back brace of claim 1 wherein the fastening means are made of VELCRO material.

3. The back brace of claim 1 wherein the struts are made of semi-flexible plastic material.

4. The back brace of claim 1 wherein the web members are flexible.

5. The back brace of claim 1 wherein there are two struts on each side of the patient's spine.

6. The back brace of claim 14 wherein the biasing means are springs which springs are disposed to urge the strut means to expand longitudinally to thereby absorb a substantial portion of the vertical impacts imparted by the upper body to the lower body as the patient walks.

7. The back brace of claim 6 wherein the struts comprise an outer tube and an inner tube telescoped within the outer tube; the springs being disposed within the tubes between a portion of the inner tube and a portion of the outer tube.

8. The back brace of claim 7 wherein the inner tube of each strut has a projection therein, said projection engaging the spring therein at a point of engagement, the point of engagement being adjustable by rotating the inner tube with respect to the outer tube.

9. The back brace of claim 8 wherein there are two struts on each side of the patient's spine.

* * * * *